(12) United States Patent
Nel

(10) Patent No.: US 8,970,219 B2
(45) Date of Patent: Mar. 3, 2015

(54) SEARCH COIL ASSEMBLY AND SYSTEM FOR METAL DETECTION

(76) Inventor: Louis Marlo Nel, Shelly Park (NZ)

(*) Notice: Subject to any disclaimer, the term of this patent is extended or adjusted under 35 U.S.C. 154(b) by 208 days.

(21) Appl. No.: 13/474,674

(22) Filed: May 17, 2012

(65) Prior Publication Data

US 2013/0307531 A1 Nov. 21, 2013

(51) Int. Cl.
*G01N 27/72* (2006.01)

(52) U.S. Cl.
USPC .......................................... 324/329; 324/326

(58) Field of Classification Search
USPC .................................................. 324/326–329
See application file for complete search history.

(56) References Cited

U.S. PATENT DOCUMENTS

| | | | |
|---|---|---|---|
| 1,624,473 A * | 4/1927 | Clement | 343/852 |
| 3,457,502 A | 7/1969 | Fletcher | |
| 3,753,185 A | 8/1973 | Mahan | |
| 4,053,828 A | 10/1977 | Ambler | |
| 4,345,208 A * | 8/1982 | Wilson | 324/329 |
| 4,970,701 A | 11/1990 | Kirkland | |
| 4,975,912 A | 12/1990 | Hogge | |
| 4,990,852 A | 2/1991 | Kirkland | |
| 5,249,162 A | 9/1993 | Kirkland | |
| 5,680,048 A * | 10/1997 | Wollny | 324/329 |
| 6,437,573 B1 * | 8/2002 | Golder et al. | 324/329 |
| 6,541,965 B1 * | 4/2003 | Binder et al. | 324/243 |
| 6,541,966 B1 * | 4/2003 | Keene | 324/243 |
| 6,822,429 B2 * | 11/2004 | Golder et al. | 324/67 |
| 7,786,731 B2 * | 8/2010 | Cole et al. | 324/326 |
| 7,999,550 B2 * | 8/2011 | Morrison et al. | 324/326 |
| 8,676,522 B2 * | 3/2014 | Pearson | 702/57 |
| 2005/0156600 A1 * | 7/2005 | Olsson et al. | 324/329 |

* cited by examiner

*Primary Examiner* — Jay Patidar

(57) ABSTRACT

A search coil assembly comprises a transmit coil operable for radiating a magnetic field in response to a time varying current. The transmit coil comprises a conductive path being disposed at least within a transmit plane for radiating the magnetic field. At least one receive coil is operable for inducting a current in response to a time varying magnetic field. The receive coil comprises a conductive path being disposed within a receive plane for inducting the current. The receive coil is positionable to place the receive plane and the transmit plane in a substantially orthogonal orientation with the receive plane being substantially within null regions of the transmit coil's magnetic field, in which a metallic object, at a distance from the search coil assembly, reacts to a radiated magnetic field from the transmit coil, and the receive coil inducts a current in response to the reaction.

20 Claims, 8 Drawing Sheets

SEARCH COIL ASSEMBLY AND SYSTEM FOR METAL DETECTION

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to metal detection devices. More particularly, one or more embodiments of the invention relate to metal detection devices for detecting elongated as well as non-elongated objects.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Metal detectors are used for many applications including detecting land mines, geophysical prospecting, treasure hunting and construction.

Some conventional wire detectors are used for detecting the presence and location of a conductor which extends on opposite sides of a water/air boundary. For example, in the case of a command control wire leading from a location on a bank of a body of water, to a mine situated in the water. These detection systems rely on the coupling between a radio frequency transmitter, which may be located some distance away or carried as a mobile unit aboard a suitable land, water or air vehicle, to couple a signal into the portion of the wire above the water. The above water portion serves as a receiving antenna, which results in the underwater portion acting as a transmitter, where the received signal is retransmitted into the surrounding water medium.

Other conventional cable and pipe locators use up to three different methods to apply a signal to the object. The conductive method applies the signal directly to one end of the cable or wire, while the other end is grounded. The inductive clamp method uses a clamp with jaws which close around the conductor to inductively couple the transmit signal into the object, while the other end is grounded. The inductive method uses a separate transmitter placed directly over the buried cable to induce a signal into any nearby conductors, and is located 13 to 15 meters away from the receiver to reduce false signals coupled through the air. These methods typically rely on the operator having direct contact with the conductor to connect a signal or clamp, or having some idea of where the conductor is buried to position the transmitter.

Some conventional orthogonal coil configurations are composed of turns of wire forming the inductor coils wrapped around a mass of material and bonded to the mass such that the coils becomes deformed responsive to the deformation of the mass. The axial height of one coil approximately equals the width of the other coil on the sides where the coils cross. A third auxiliary coil with some form of external adjustment is used to reduce the coupling between the transmit coil and receive coil to achieve a balanced condition. The three coils are typically of the same size and shape. The wide cross sectional area of the transmit coil produces a weak magnetic field across a wide area.

Elongated objects which have a small cross sectional areas and minimal metallic content, in particular landmine tripwires, are often difficult to detect and to determine the location of De-mining teams face considerable danger when trying to locate tripwire activated landmine wires, as the tripwires are typically located above the ground and may be obscured from vision by foliage. Conventional methods used to indicate the presence of tripwires concealed by foliage include the use of a feeler stick used to prod into the foliage and slowly raised to feel for the presence of a tripwire.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
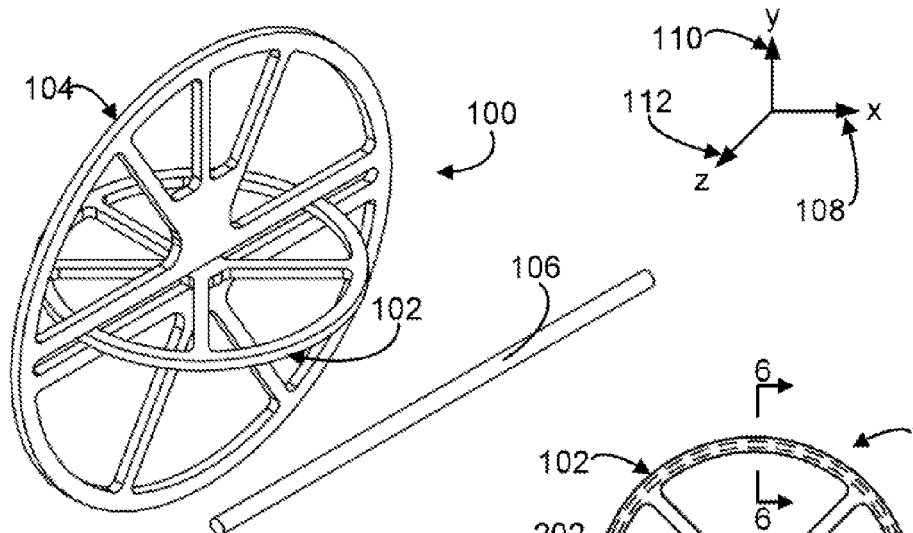
FIG. 1 illustrates an example search coil assembly, in accordance with an embodiment of the present invention.

Unless otherwise indicated illustrations in the figures are not necessarily drawn to scale.

DETAILED DESCRIPTION OF SOME EMBODIMENTS

Embodiments of the present invention are best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

"Software" may refer to prescribed rules to operate a computer. Examples of software may include: code segments in one or more computer-readable languages; graphical and or/textual instructions; applets; pre-compiled code; interpreted code; compiled code; and computer programs.

A "computer-readable medium" may refer to any storage device used for storing data accessible by a computer. Examples of a computer-readable medium may include: a magnetic hard disk; a floppy disk; an optical disk, such as a CD-ROM and a DVD; a magnetic tape; a flash memory; a memory chip; and/or other types of media that can store machine-readable instructions thereon.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

A non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; however, the non-transitory computer readable medium does not include a pure transitory signal per se.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Embodiments of the present invention will be described which provide means and methods for a metal detector and metal detector coil configuration which display a high degree of sensitivity to narrow, elongated type objects such as landmine tripwires, and a method with which to determine the location and position of these objects.

Prefabricated inductor coils are supported by separate rigid structures and assembled together to produce the final coil assembly. In a non-limiting example, during assembly, a continuous time-varying current is applied to the transmitting coil, while the receive coil's output is monitored using an AC meter or oscilloscope. The coil housings are translated and rotated relative to each other to achieve the lowest output signal from the receive coil, which indicates that a balanced or null condition has been achieved. The housings are then secured to maintain the balanced condition. The balancing is performed with the absence of any objects which may disturb the magnetic field.

The metal detector generates a continuous time-varying current. The time-varying current is applied to the transmitting coil which generates the primary magnetic field and induces currents in nearby metallic objects. The induced eddy currents generate a weak secondary magnetic field which has a different amplitude and phase as compared to the primary magnetic field, and can be detected by a suitable receive coil and detector circuitry.

The coils are positioned in order to reduce the coupling between the coils and achieve a balanced or null condition. Furthermore, a low magnetic coupling is provided between the coils in the absence of objects which disturb the magnetic field. The degree and stability to which the coils are decoupled in an object-free environment provides increased sensitivity and detection range for the device.

The wire or conductor detection method and apparatus used by the metal detection device aims to provide a portable device which has the ability to detect elongated type objects such as landmine tripwires, at ranges exceeding 500 mm. Furthermore, the metal detector may be configured for detecting objects such as, but not limited to, nails or pipes located within walls, metal reinforcing bar encased in concrete, or wires or pipes located above or below the surface of the ground. The device may also be configured for detecting metallic objects which located within organisms such as, but not limited to, humans, animals or plants. Furthermore, the device may be configured for detecting and distinguishing between dissimilar metals, for example, but not limited to, a copper evaporator coil located inside a refrigerator made from mild steel, or a brass fitting connected to a copper pipe. However, the metal detection device is not limited to detecting elongated type objects or metallic objects, and may be used to detect any objects which disturb the magnetic field.

The metal detector coil configuration generates a strong magnetic field in a narrow area, which induces large signals in elongated type conductors and allows for the receive coil to be positioned substantially within the null of the transmit coil's magnetic field. This reduces the magnetic coupling between the coils which increases the sensitivity of the device, while making it easier to initially balance the coils during construction.

The metal detector coil configuration provides high sensitivity to elongated type conductors making it possible to detect landmine tripwires.

The metal detector performs detection via detected changes in the amplitude and/or phase of the received signal, relative to a reference signal, when an object's positional location changes from above the plane of the transmit coil to below the plane and vice versa. This improves the ability of the operator to accurately determine the location of the elongated object. Furthermore, metals which have different electrical and magnetic properties produce different amplitudes and phase characteristics, relative to the reference signal, when the object's positional location remains unchanged relative to the plane of the transmit coil. This enables the operator to distinguish between objects which have different properties, for example copper pipe and steel reinforcing bar.

The metal detector coil configuration provides the capability to determine the location and position of elongated type objects. This is achieved by moving the device above and below the object, and by rotating the device with respect to the object producing a change in the amplitude and or phase of the received signal.

The metal detector coil configuration provides the capability to operate in areas where high levels of extraneous EMI exists while maintaining a high level of sensitivity. The use of two receive coils reduces the susceptibility to extraneous interference sources by treating these sources as a signal common to both receive coils. The differential signal between the receive coils is used to detect the object, and to determine the location and position of the object relative to the search coil assembly.

The metal detector coil configuration provides the capability to detect and determine the location of other types of elongated objects; which may be located beneath the ground or in a wall behind plasterboard or gypsum board such as pipes or cables not having direct access, or encased in concrete such as steel reinforcing bar.

The metal detector is configured with a transmit coil as a means for generating a magnetic field in the vicinity of the metallic object, and a receive coil as a means for detection of the secondary magnetic field produced by the object. In some embodiments the receive coil is larger in diameter than the transmit coil and vice-versa. The two coils are formed as an induction coil derived from a plurality of turns of insulated wire, wound such that they enclose a small cross sectional area. In some embodiments, the coils are covered in an insulating material and a conductive layer which acts as a shield. The coils are enclosed within separate housing structures. Furthermore, the coils are positioned such that the transmit coil's plane is positioned substantially in an orthogonal relationship with the receive coil's plane. The receive coil is positioned within the null of the transmit coil's magnetic field with minimal overlapping area between the windings where the coils cross. The transmit coil is connected to a time-varying current source as a means to generate a magnetic field. The receive coil is connected to a suitable receiver as a means to detect objects which disturb the magnetic field.

In other embodiments the circular receive coil and housing is replaced with a housing which is configured of two, semi-circular receive coils. The semi-circular receive coils are positioned within the same plane, and positioned above and below the plane of the transmit coil in an orthogonal relationship to the transmit coil. In other embodiments the two semi-circular receive coils are positioned in the same plane and in an overlapping configuration, positioned above and below the plane of the transmit coil forming an orthogonal relationship.

FIG. 1 illustrates an example search coil assembly, in accordance with an embodiment of the present invention.

A search coil assembly 100 includes a transmit coil housing 102 and a receive coil housing 104.

Search coil assembly lies in three-dimensional space defined by an x-axis 108, a y-axis 110 and a z-axis 112. With an x-y plane defined by x-axis 108 and y-axis 110, a y-z plane defined by y-axis 110 and z-axis 112 and a x-z plane defined by x-axis 108 and z-axis 112.

Transmit coil housing 102 is oriented with respect to the x-z plane and receive coil housing 104 is oriented with respect to the y-z plane.

Transmit coil housing 102 is inserted into and connected to receive coil housing 104 with transmit coil housing 102 positioned orthogonal to receive coil housing 104.

Search coil assembly 100 may be used for performing metal detection.

Transmit coil housing 102 may be used for emitting a magnetic field. As a non-limiting example, transmit coil housing 102 may be configured as a circular housing and may be configured of a non-conductive material. Transmit coil housing 102 provides a rigid structure for providing support for inductor coils. As a non-limiting example, the non-conductive material may be a resin impregnated composite material such as fiberglass. As a further non-limiting example, the non-conductive material may be a thermoplastic polymer such as acrylonitrile butadiene styrene (ABS) or polycarbonate.

Receive coil housing 104 may be used for receiving a magnetic field. As a non-limiting example, receive coil housing 104 may be configured as a circular housing and may be configured of a non-conductive material. Receive coil housing 104 provides a rigid structure for support of inductor coils. As a non-limiting example, the non-conductive material may be a resin impregnated composite material such as fiberglass. As a further non-limiting example, the non-conductive material may be a thermoplastic polymer such as acrylonitrile butadiene styrene (ABS) or polycarbonate.

Receive coil housing 104 is larger in diameter than transmit coil housing 102.

Search coil assembly 100 provides detection of objects. As a non-limiting example, search coil assembly 100 is able to detect metal objects. Furthermore, as a non-limiting example, search coil assembly 100 is able to detect elongated objects. Non-limiting examples for elongated objects include wires, pipes and nails.

Transmit coil housing 102 and receive coil housing 104 are positioned in a perpendicular or orthogonal relationship.

In operation, transmit coil housing 102 emits a magnetic field. An object 106 receives the magnetic field transmitted by transmit coil housing 102. As a result of receiving the magnetic field, eddy currents are produced in object 106 which results in object 106 emitting a magnetic field. Receive coil housing 104 receives the magnetic field generated by object 106.

FIG. 1 illustrates an example search coil assembly used for performing metal detection via transmission of a magnetic field and reception of a returned version of the transmitted magnetic field.

Figure 2A:
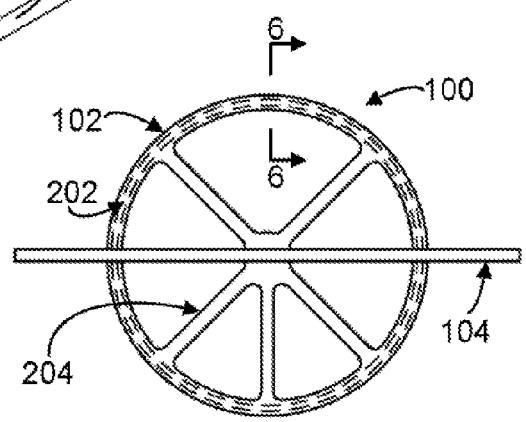
FIG. 2A is a top view illustrating the example search coil assembly as described with reference to FIG. 1, in accordance with an embodiment of the present invention.

FIG. 2A is a top view illustrating the example search coil assembly as described with reference to FIG. 1, in accordance with an embodiment of the present invention.

Transmit coil housing 102 includes a transmit coil 202 and a multiplicity of spokes with a sampling noted as a spoke 204.

Transmit coil 202 is enclosed within transmit coil housing 102. Transmit coil 202 is configured at or near the center of receive coil housing 104.

Spoke 204 provides support and structure for transmit coil housing 102.

FIG. 2A is a top view illustrating the example search coil assembly as described with reference to FIG. 1 where the receive coil is larger in diameter than the transmit coil.

Figure 2B:
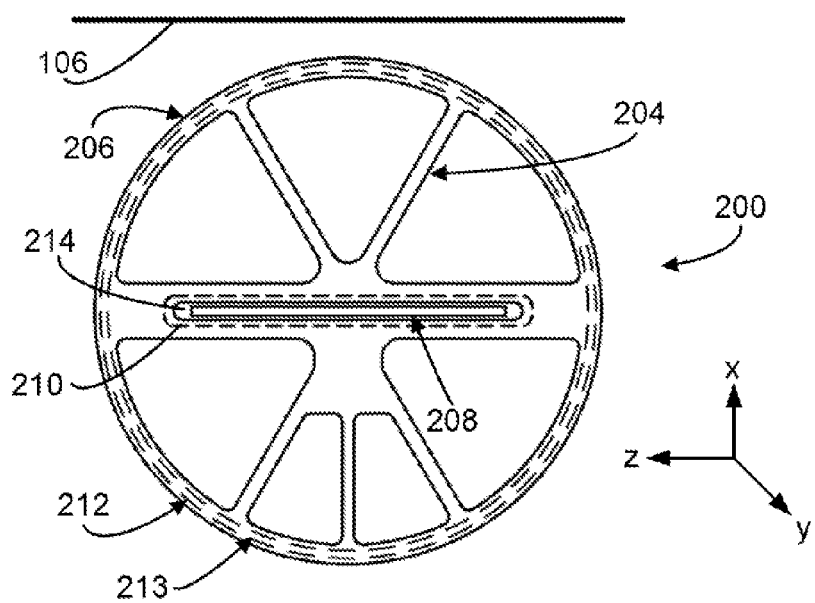
FIG. 2B is a top view illustrating the example search coil assembly as described with reference to FIG. 1, in accordance with an embodiment of the present invention.

FIG. 2B is a top view illustrating an alternative embodiment of the example search coil assembly as described with reference to FIG. 1, in accordance with an embodiment of the present invention.

A search coil assembly 200 includes a transmit coil housing 206 and a receive coil housing 208. Receive coil housing 208 is inserted into and connected to transmit coil housing 206. Receive coil housing 208 is oriented orthogonal to transmit coil housing 206.

Search coil assembly 200 may be used for performing metal detection.

Transmit coil housing 206 may be used for emitting a magnetic field.

Receive coil housing 208 may be used for receiving a magnetic field.

Transmit coil housing 206 is larger in diameter than receive coil housing 208.

A magnetic shielding material 210 may be used for reducing the magnetic coupling between the transmit coil 213 and the receive coil 310.

A conductive layer 212 operates as a Faraday shield. A Faraday shield is an enclosure formed by a conducting material or by a mesh of conducting material. Conductive layer 212 may be configured in single or multiple layers as needed for shielding and is connected to circuit ground. Non-limiting examples for conductive layer 212 include electrical shielding tape, copper tape and shielding paint. In other embodiments conductive layer 212 may be omitted. Conductive layer 212 is configured such that it does not form a full electrical loop. As a non-limiting example, the ends of conductive layer 212 may be separated by a small air gap. In other embodiments, the ends of the conductive layer 212 may overlap each other, but are separated by an insulation layer.

A transmit coil 213 is enclosed within transmit coil housing 206. An opening 214 is surrounded by magnetic shielding material 210.

In other embodiments, magnetic shielding material 210 may be omitted.

Receive coil housing 208 is positioned in opening 214. Furthermore, receive coil housing 208 is configured in an orthogonal relationship with transmit coil housing 206.

In operation, search coil assembly 200 functions in a similar manner as search coil assembly 100 described with reference to FIG. 1.

FIG. 2B is a top view illustrating an alternative embodiment of the example search coil assembly as described with reference to FIG. 1 where the diameter of the transmit coil housing is larger than the receive coil housing.

Figure 3A:
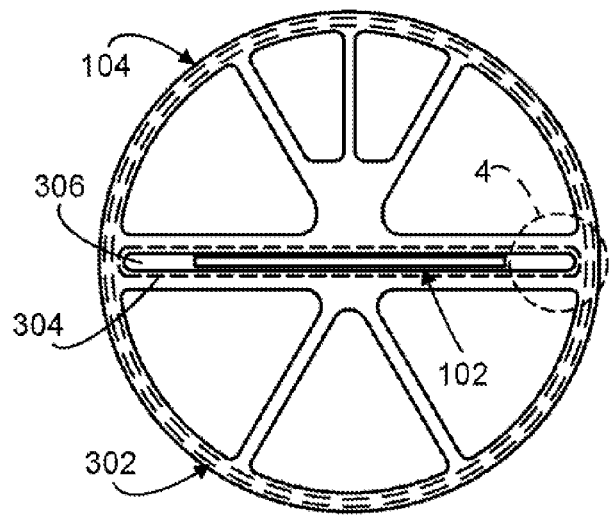
FIG. 3A is a rear view illustrating the example receive coil as described with reference to FIG. 1, in accordance with an embodiment of the present invention.

FIG. 3A is a rear view illustrating the example receive coil as described with reference to FIG. 1, in accordance with an embodiment of the present invention.

Receive coil housing 104 includes a receive coil 302 and a magnetic shield material 304.

Receive coil 302 receives a magnetic field.

Magnetic shield material 304 provides a path for the magnetic field lines around the shielded volume. Magnetic shield material 304 may be configured of metal alloys which display high magnetic permeability properties. Non-limiting examples of metal alloys are Mu-Metal, Permalloy, Co-Netic or Netic shielding films and Nanovate-EM coatings. Mu-Metal shielding film has high magnetic permeability and is typically configured of approximately 77% nickel, 16% iron, 5% copper and 2% chromium or molybdenum.

An opening 306 is located within receive coil housing 104 for receiving transmit coil housing 102.

Transmit coil housing 102 is positioned within opening 306. Furthermore, magnetic shield material 304 is positioned inside a cavity located within receive coil housing 104 and adjacent to opening 306.

Receive coil 302 is enclosed within receive coil housing 104.

Magnetic shield material 304 may be used to further reduce the magnetic coupling between transmit coil 202 described with reference to FIG. 2A and receive coil 302.

In other embodiments, magnetic shield material 304 may be positioned within a cavity adjacent to receive coil 302. Furthermore, in other embodiments, a magnetic shield coating such as Nanovate-EM may be applied to part of the housing structure adjacent to the opening to provide the magnetic shielding 304. Furthermore, in other embodiments magnetic shield material 304 and cavity may be omitted.

Fabrication of receive coil housing 104 is performed in a similar manner as transmit coil housing 102, with the exception that receive coil housing 104 is configured with opening 306. Opening 306 is provided in order to secure transmit coil housing 102. Receive coil 302 is shielded with a conductive layer (e.g. Faraday shield) and connected to circuit ground. A cavity may also be provided in order to configure magnetic shield material 304.

FIG. 3A is a rear view illustrating the receive coil as described with reference to FIG. 1 where a magnetic shield material resists penetration by magnetic fields.

Figure 3B:
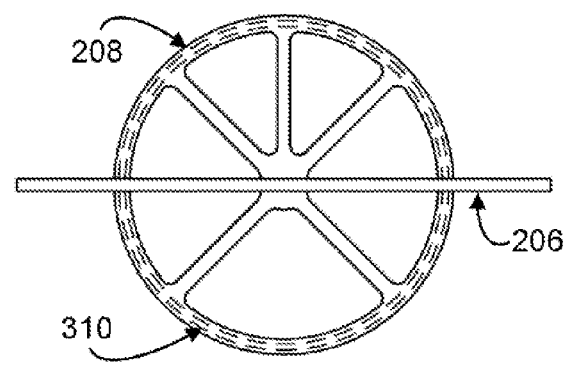
FIG. 3B is a rear view illustrating the example receive coil as described with reference to FIG. 1, in accordance with an embodiment of the present invention.

FIG. 3B is a rear view illustrating the example receive coil as described with reference to FIG. 1, in accordance with an embodiment of the present invention.

A receive coil 310 is enclosed within receive coil housing 208. Receive coil housing 208 is inserted into transmit coil housing 206 where diameter of receive coil housing 208 is smaller than the diameter of transmit coil housing 206.

In other embodiments, two semi-circular receive coils are positioned above and below the plane traversing transmit coil housing 206. Furthermore, in other embodiments, two overlapping semi-circular receive coils positioned above and below the plane traversing transmit coil housing 206.

Receive coil housing 208 operates in a similar manner as described with reference to receive coil housing 104 described with reference to FIG. 1.

FIG. 3B is a rear view illustrating the example receive coil as described with reference to FIG. 1, where the diameter of the receive coil housing is smaller than the diameter of the transmit coil housing.

Figure 4:
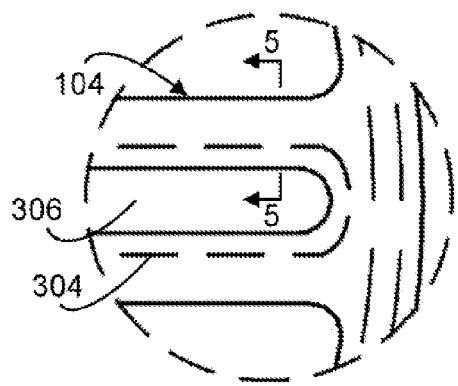
FIG. 4 illustrates location for a cross sectional view, as presented by FIG. 5 below, for example receive coil housing as described with reference to FIG. 3A, in accordance with an embodiment of the present invention.

FIG. 4 illustrates an enlarged view of a portion of a location for a cross sectional view, as presented by FIG. 5 below, for example receive coil housing 104 as described with reference to FIG. 3A, in accordance with an embodiment of the present invention.

Figure 5:
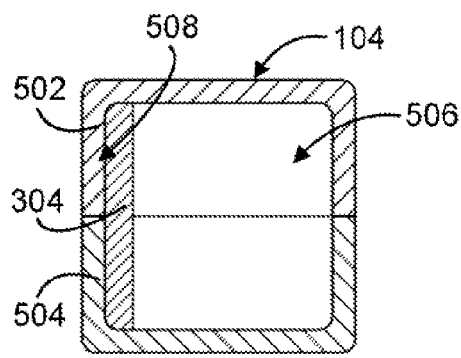
FIG. 5 is a cross-sectional view of a portion of the example receive coil housing taken along the line 5-5 of FIG. 4, in accordance with an embodiment of the present invention.

FIG. 5 is a cross-sectional view of a portion of the example receive coil housing taken along the line 5-5 of FIG. 4, in accordance with an embodiment of the present invention.

Receive coil housing 104 includes an upper half 502 and a lower half 504.

Upper half 502 and lower half 504 are joined together and provide a cavity 506.

Magnetic shield material 304 is located within cavity 506 and configured against a wall 508 formed by upper half 502 and lower half 504.

FIG. 5 is a cross-sectional view of a portion of the receive coil housing taken along the line 5-5 of FIG. 4 where a magnetic shield material is located within the receive coil housing.

Figure 6:
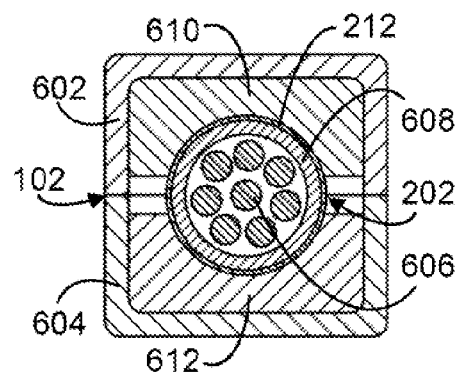
FIG. 6 is a cross-sectional view of the example transmit coil and transmit coil housing taken along line 6-6 of FIG. 2A, in accordance with an embodiment of the present invention.

FIG. 6 is a cross-sectional view of the example transmit coil and transmit coil housing taken along line 6-6 of FIG. 2A, in accordance with an embodiment of the present invention.

Transmit coil housing 102 is formed by a top housing half 602 and a bottom housing half 604. Top housing half 602 and bottom housing half 604 may be secured by any known means. Non-limiting examples for securing the halves include adhesive and plastic welding. Non-limiting examples for a housing to support transmit coil 202 (FIG. 2A) or receive coil 302 (FIG. 3A), is a housing made from two halves, a housing with a groove within which the coil is located, or a flat housing on which the coil is secured, or a combination of the housing types.

Transmit coil windings 606 are located within an insulation layer 608. Furthermore, in other embodiments, insulation layer 608 may be omitted. Furthermore, in other embodiments, coil windings 606 instead may be a single coil.

Insulation layer 608 is configured between an isolation pad 610 and an isolation pad 612.

Transmit coil windings 606, insulation layer 608, isolation pad 610 and isolation pad 612 are configured within transmit coil housing 102.

Transmit coil 202 is configured of multiple turns of transmit coil windings 606. Non-limiting examples for transmit coil windings 606 include insulated solid copper wire and multi-strand Litz wire. Litz wire is a type of cable used for carrying alternating current. Litz wire is designed to reduce skin effect and proximity effect losses in conductors.

Transmit coil windings 606 are enclosed in insulation layer 608. As a non-limiting example, insulation layer 608 may be configured of polytetrafluoreothylene (PTFE), polyethylene, or polypropylene. PTFE exhibits a low relative permittivity value which aids in reducing the capacitive coupling between transmit coil 202 and conductive layer 212 described with reference to FIG. 2B.

Transmit coil 202 is thermally isolated from transmit coil housing 102 via isolation pad 610 and isolation pad 612. Isolation pad 610 is located within top housing half 602 and isolation pad 612 is located within bottom housing half 604. Isolation pad 610 and isolation pad 612 support and restrain transmit coil 202 within transmit coil housing 102. As a non-limiting example, isolation pad 610 and isolation pad 612 may be configured of a thermally stable elastomer material. Non-limiting examples for elastomer material include ethylene vinyl acetate (EVA). Additionally, further non-limiting examples for isolation pad 610 and isolation pad 612 include polyethylene (PE) foam rubber, potting compound and encapsulating compound. Furthermore, in other embodiments, isolation pads 610 and 612 may be omitted.

FIG. 6 is a cross-sectional view of the transmit coil and transmit coil housing taken along line 6-6 of FIG. 2A where transmit coil windings, insulation layer and isolation pads are configured within the transmit housing.

Figure 7:
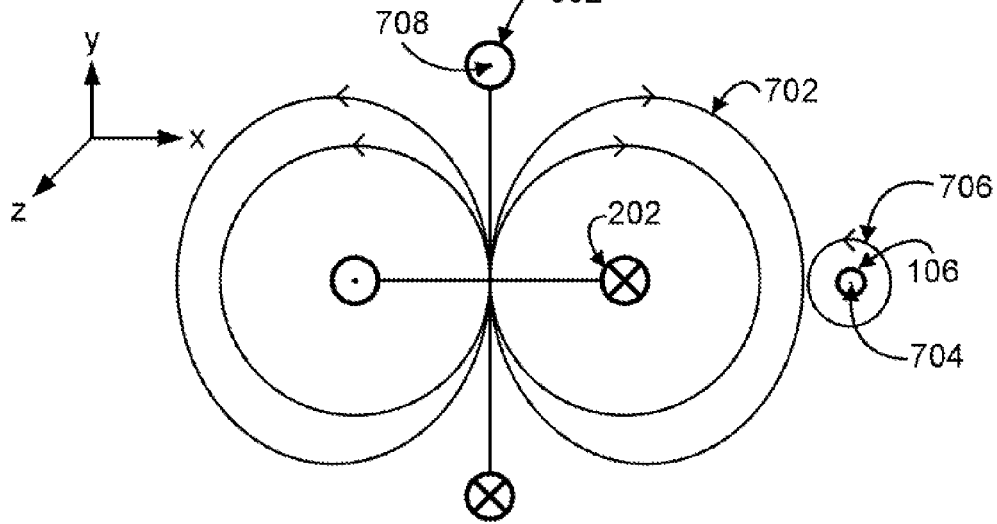
FIG. 7 illustrates the lines of flux of the magnetic field generated by the example transmit coil with the page oriented as the x-y plane as presented in FIG. 1, in accordance with an embodiment of the present invention.

FIG. 7 illustrates the lines of flux of the magnetic field generated by the example transmit coil with the page oriented as the x-y plane as presented in FIG. 1, in accordance with an embodiment of the present invention.

Transmit coil 202 is wound such that it is enclosed within a small cross sectional area in order to create a strong magnetic field across a narrow area in the vicinity of object 106. The small cross sectional area improves the ability to induce large signals in objects having a small cross sectional area (e.g. object 106).

Transmit coil 202 receives an electrical current which generates a magnetic flux lines 702. Object 106 receives magnetic flux lines 702 and an eddy current 704 is created. Eddy current 704 generates a magnetic flux lines 706. Receive coil 302 receives magnetic flux lines 706 and generates an electrical current 708.

A large signal is induced in object 106 when positioned in the same plane and at a tangent to transmit coil 202.

Receive coil 302 is also enclosed within a small cross-sectional area enabling receive coil 302 to be positioned substantially within the nulls of the magnetic field and present a small overlapping side area located between the conductors of transmit coil 202 and receive coil 302. This small overlapping side area located between the conductors of transmit coil 202 and receive coil 302 enable receive coil 302 to be located within an area of low magnetic flux density which reduces the magnetic coupling between transmit coil 202 and receive coil 302 and improves the sensitivity. Furthermore, this makes it easier for initial balancing of transmit coil 202 and receive coil 302. Furthermore, this reduces the effects of thermal expansion and movement of the coils associated with operation of a handheld detection device.

FIG. 7 illustrates the lines of flux of the magnetic field generated by the transmit coil, received by an object with object generating return magnetic flux lines.

Figure 8:
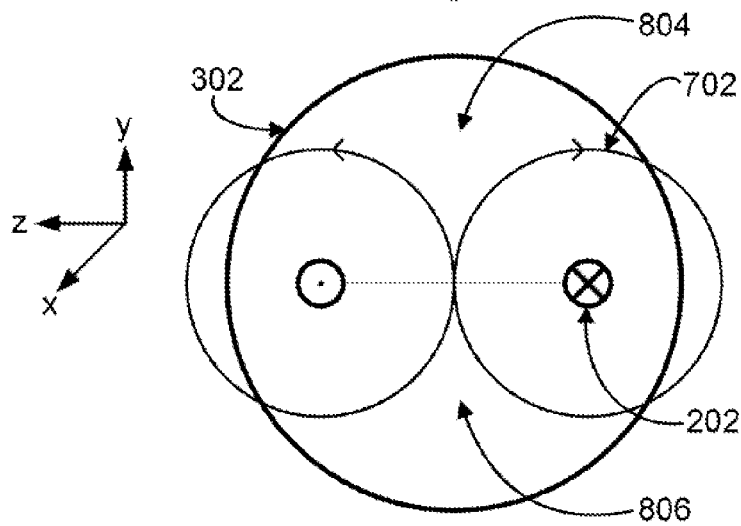
FIG. 8 illustrates the lines of flux of the magnetic field generated by the example transmit coil with the page oriented as the y-z plane as presented in FIG. 1, in accordance with an embodiment of the present invention.

FIG. 8 illustrates the lines of flux of the magnetic field generated by the example transmit coil with the page oriented as the y-z plane as presented in FIG. 1, in accordance with an embodiment of the present invention.

A significant portion of receive coil 302 is located within an upper null region 804 and in a lower null region 806. This configuration enables a significant decoupling of receive coil 302 from magnetic flux lines 702 generated by transmit coil 202.

The portion of magnetic flux lines 702 located outside of the upper null region 804 and lower null region 806 are predominately located within the same plane as receive coil 302. Furthermore, magnetic shield material 304, as described with reference to FIG. 3A, provides reduction of the magnetic field located outside of the null regions.

FIG. 8 illustrates the lines of flux of the magnetic field generated by the transmit coil with significant portions of the receive coil located in the null regions of the lines of flux associated with the magnetic field.

Figure 9:
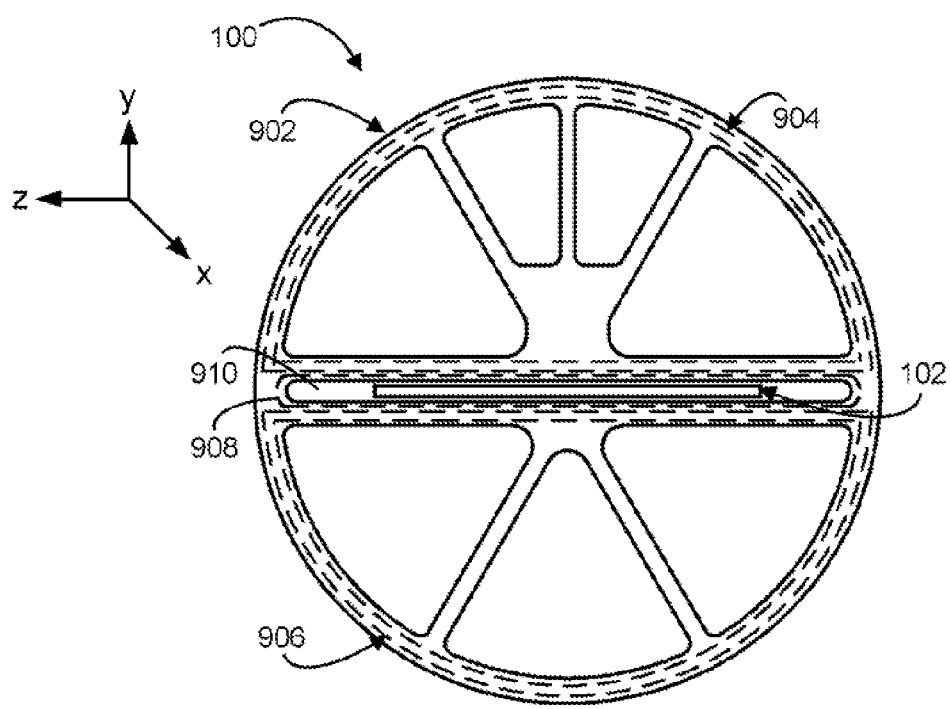
FIG. 9 illustrates a view an alternative embodiment of the example search coil assembly with the page oriented as the y-z plane as presented in FIG. 1, in accordance with an embodiment of the present invention.

FIG. 9 illustrates a view an alternative embodiment of the example search coil assembly with the page oriented as the y-z plane as presented in FIG. 1, in accordance with an embodiment of the present invention.

Search coil assembly 100 includes a receive coil housing 902 and transmit coil housing 102. The receive coil housing 902 is larger in diameter than the transmit coil housing 102. In other embodiments the receive coil housing 902 may be smaller in diameter than transmit coil housing 102 as previously described with reference to FIG. 2B.

Receive coil housing 902 includes an upper receive coil 904 and a lower receive coil 906.

A magnetic shielding material 908 is configured within a cavity located within receive coil housing 902.

Magnetic shielding material 908 surrounds an opening 910.

Upper receive coil 904 receives a magnetic field received by the upper portion of receive coil housing 902 and lower receive coil 906 receives a magnetic field received by the lower portion of receive coil housing 902.

Magnetic shielding material 908 reduces the magnetic coupling between the transmit coil 202 and the receive coils 904 and 906.

In an embodiment shown in FIG. 9, upper receive coil 904 and lower receive coil 906 are configured as semi-circular coils. In other embodiments the receive coils may be other geometric shapes, non-limiting examples are square or elliptically shaped coils. Upper receive coil 904 and lower receive coil 906 are located within receive coil housing 902.

Upper receive coil 904 and lower receive coil 906 are coplanar and positioned above and below opening 910, respectively. Upper receive coil 904 and lower receive coil 906 are configured such that the planes traversing the devices are substantially orthogonal to the plane traversing transmit coil housing 102.

Magnetic shielding material 908 is located within a cavity located internal to receive coil housing 902. Furthermore, cavity is located adjacent to opening 910.

In other embodiments, magnetic shielding material 908 and cavity 910 may be omitted.

Search coil assembly 100 configured with receive coil housing 902 operates in a similar manner as described previously for determining the location of an object. Transmit coil 202 is connected to a time-varying current source for generating a magnetic field. Upper receive coil 904 and lower receive coil 906 are connected as separate inputs to a receiver. The receiver circuitry detects changes in the amplitude and/or phase of the received signals. Furthermore, the receiver circuitry detects the differential signal between upper receive coil 904 and lower receive coil 906 for aiding in determining the location of an object.

When an object is located above the plane traversing transmit coil 202, a larger signal is produced by upper receive coil 904 located above the plane. Furthermore, when an object is located below the plane traversing transmit coil 202, a larger signal is produced by lower receive coil 906.

In other embodiments, upper receive coil 904 and lower receive coil 906 may be configured in a series-opposing polarity and configured for supplying a single signal to the receiver. When connected to a single input, the receiver circuitry detects changes in the amplitude and/or phase of the received signal associated with the received magnetic field.

The implementation of two receive coils as opposed to one receive coil as discussed previously, reduces the susceptibility to increased levels of extraneous Electromagnetic Interference (EMI), as a result of the interference being considered as a common mode signal.

FIG. 9 illustrates a view an alternative embodiment of the search coil assembly configured with two receive coils.

Figure 10:
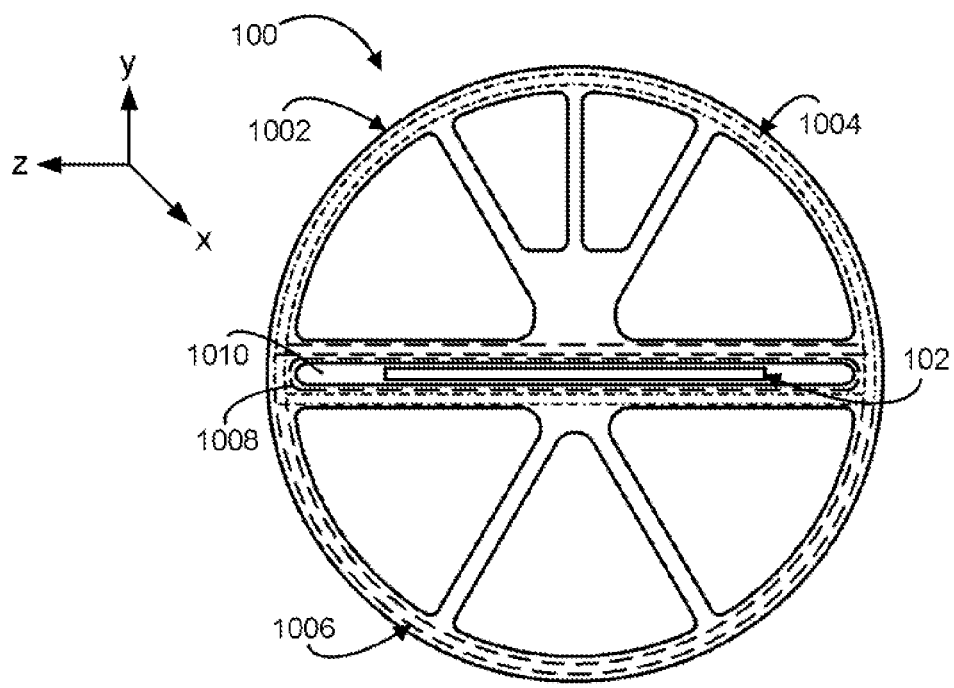
FIG. 10 illustrates a view an alternative embodiment of the search coil assembly with the page oriented as the y-z plane as presented in FIG. 1, in accordance with an embodiment of the present invention.

FIG. 10 illustrates a view of an alternative embodiment of the example search coil assembly with the page oriented as the y-z plane as presented in FIG. 1, in accordance with an embodiment of the present invention.

Search coil assembly 100 includes a receive coil housing 1002 and transmit coil housing 102. The receive coil housing 1002 is larger in diameter than the transmit coil housing 102. In other embodiments the receive coil housing 1002 may be smaller in diameter than transmit coil housing 102 as previously described with reference to FIG. 2B.

Receive coil housing 1002 includes an upper receive coil 1004 and a lower receive coil 1006.

A magnetic shielding material 1008 is configured within a cavity located within receive coil housing 1002.

Magnetic shielding material 1008 surrounds an opening 1010.

Upper receive coil 1004 and lower receive coil 1006 overlap in the regions adjacent to opening 1010.

Upper receive coil 1004 receives a magnetic field received by the upper portion of receive coil housing 1002 and lower receive coil 1006 receives a magnetic field received by the lower portion of receive coil housing 1002.

Magnetic shielding material 1008 reduces the magnetic coupling between the transmit coil 202 and the receive coils 1004 and 1006.

In an embodiment shown in FIG. 10, upper receive coil 1004 and lower receive coil 1006 are configured as semi-circular coils and are positioned to overlap in the area adjacent to opening 1010. In other embodiments the receive coils may be other geometric shapes, non-limiting examples are square or elliptically shaped coils.

Receive coil housing 1002 is configured such that the plane traversing receive coil housing 1002 is substantially orthogonal to transmit coil housing 102.

Magnetic shielding material 1008 is located within a cavity located internal to receive coil housing 1002. Furthermore, magnetic shielding material 1008 is located adjacent to opening 1010.

In other embodiments, magnetic shielding material 1008 and cavity may be omitted.

Search coil assembly 100 configured with receive coil housing 1002 operates in a similar manner as described previously for determining the location of an object. Transmit coil 202 is connected to a time-varying current source for generating a magnetic field. Upper receive coil 1004 and lower receive coil 1006 are connected as separate inputs to a receiver. The receiver circuitry detects changes in the amplitude and/or phase of the received signals. Furthermore, the receiver circuitry detects the differential between upper receive coil 1004 and lower receive coil 1006 for aiding in determining the location of an object.

When an object is located above the plane traversing transmit coil 202, a larger signal is produced by upper receive coil 1004 located above the plane. Furthermore, when an object is located below the plane traversing transmit coil 202, a larger signal is produced by lower receive coil 1006.

In other embodiments, upper receive coil 1004 and lower receive coil 1006 may be configured in a series-opposing polarity and configured for supplying a single signal to the receiver. When connected to a single input, the receiver circuitry detects changes in the amplitude and/or phase of the received signal associated with the received magnetic field.

The implementation of two receive coils as opposed to one receive coil as discussed previously, reduces the susceptibility to increased levels of extraneous Electromagnetic Interference (EMI), as a result of the interference being considered as a common mode signal.

FIG. 10 illustrates a view of an alternative embodiment of the example search coil assembly configured with two overlapping receive coils.

Figure 11:
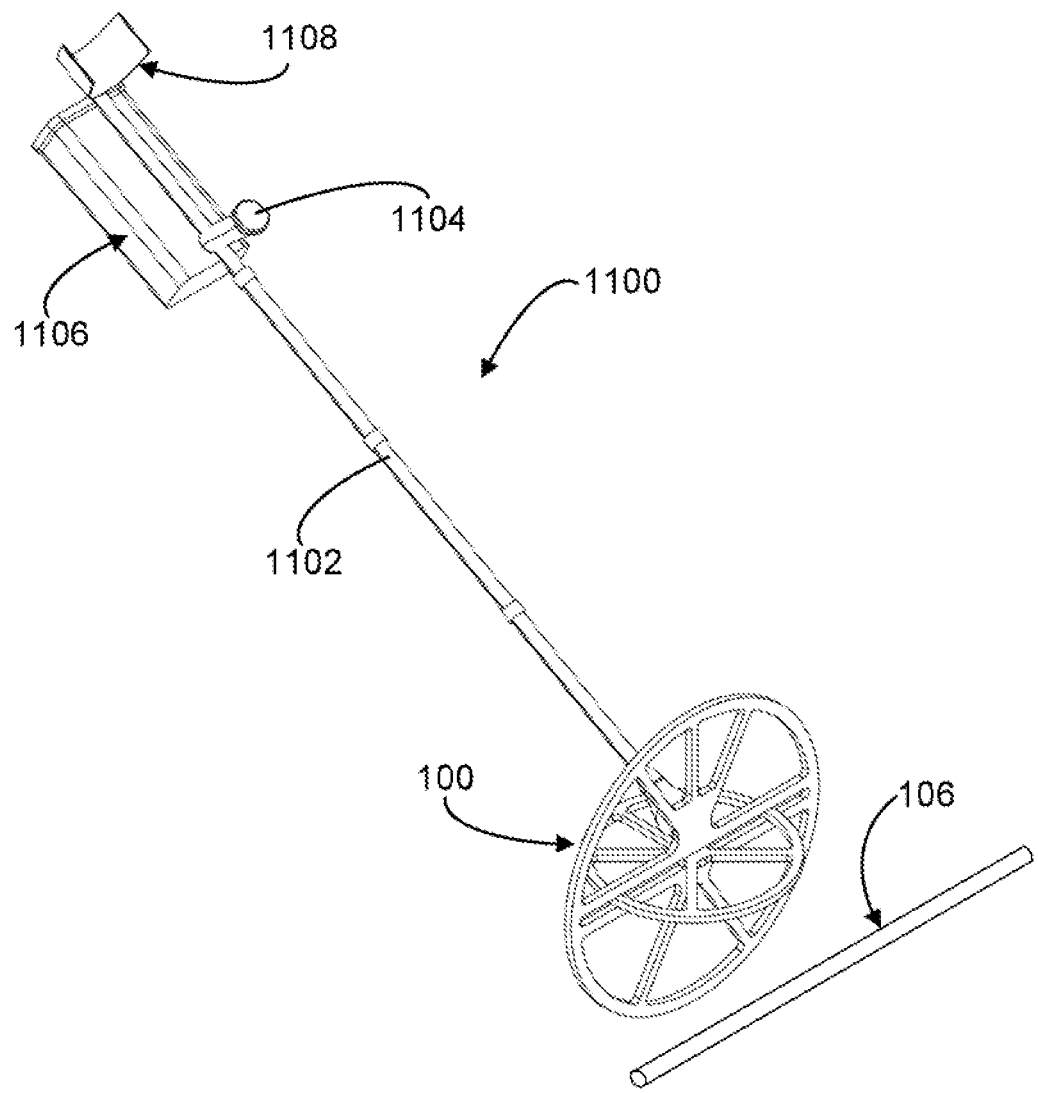
FIG. 11 illustrates an example handheld detector device incorporating the search coil assembly, in accordance with an embodiment of the present invention.

FIG. 11 illustrates an example handheld detector device incorporating the search coil assembly, in accordance with an embodiment of the present invention.

A handheld detector device 1100 includes search coil assembly 100, a shaft 1102, a handle 1104, a control enclosure 1106, an arm cuff 1108, and pivoting joint 1110

Search coil assembly 100 transmits and receives magnetic fields.

Shaft 1102 provides and extension of search coil assembly 100 from handle 1104, control enclosure 1106 and arm cuff 1108. As a non-limiting example, the shaft 1102 may be connected directly to the search coil assembly 100, or in other examples include the use of a suitable pivoting joint 1110.

Handle 1104 provides capability for gripping with a person's hand.

Control enclosure 1106 provides a structure for enclosing electronic and mechanical components for operating handheld detector device 1100.

Arm cuff 1108 provides support for a person's arm.

Search coil assembly 100, handle 1104, control enclosure 1106 and arm cuff 1108 are attached to shaft 1102.

Control enclosure 1106 provides an enclosure for control elements and electronic devices and components associated with handheld detector device 1100.

Electronic devices and components located internal to control enclosure 1106 communicate with search coil assembly 100 via a cable. As a non-limiting example, cable may be configured as a shielded cable.

In other embodiments, elements associated with control enclosure 1106 and search coil assembly 100 may be contained within a single housing.

As a non-limiting example, handheld detector device 1100 may configured as an inductively balanced metal detector. In other embodiments, handheld detector device 1100 may be configured using a pulse induction detector circuit. Pulse induction detector devices transmit a high-voltage signal pulse into the area associated with searching for objects.

As a non-limiting example, handheld detector device 1100 operates as a metal detector. Other non-limiting examples of uses for detection using handheld detector device 1100 include magnetic non-metallic materials, magnetic non-conduction materials (e.g. ferrites), conducting non-magnetic materials and conduction non-metallic materials (e.g. carbon and some liquids).

Search coil assembly 100 may be configured with circular and semi-circular coils and in other embodiments search coil assembly 100 may be configured with other geometric shapes. Non-limiting examples for other geometric shapes associated with coils include square, rectangular, elliptical and semi-elliptical.

As a non-limiting example, handheld detector device 1100 may be configured with spokes used for portions of the structure for search coil assembly 100. Furthermore, spoke implementations may be used for larger diameter coils in order to reduce weight. As a non-limiting example, a solid disk-like configuration may be used instead of spokes for smaller coils.

In operation, handle 1104 is gripped by a person's hand. Arm attached to hand gripping handle is supported by arm cuff 1108. Electronic devices located within control enclosure 1106 communicate information to search coil assembly 100 via wires (not shown) located within shaft 1102. Search coil assembly 100 receives information generated by control enclosure 1106 and transmits a magnetic field (not shown). Object 106 receives transmitted magnetic field and converts magnetic field to eddy currents (not shown). Eddy currents generate a magnetic field (not shown) received by search coil assembly 100. Search coil assembly 100 communicate an electrical signal associated with the received magnetic field to control enclosure 1106 via wires (not shown) located within shaft 1102. Control enclosure 1106 receives and processes the received electrical signal and presents information associated with the received signal (e.g. beeping sound).

FIG. 11 illustrates a handheld detector device incorporating the search coil assembly where the presence of an object is detected and presented.

Figure 12:
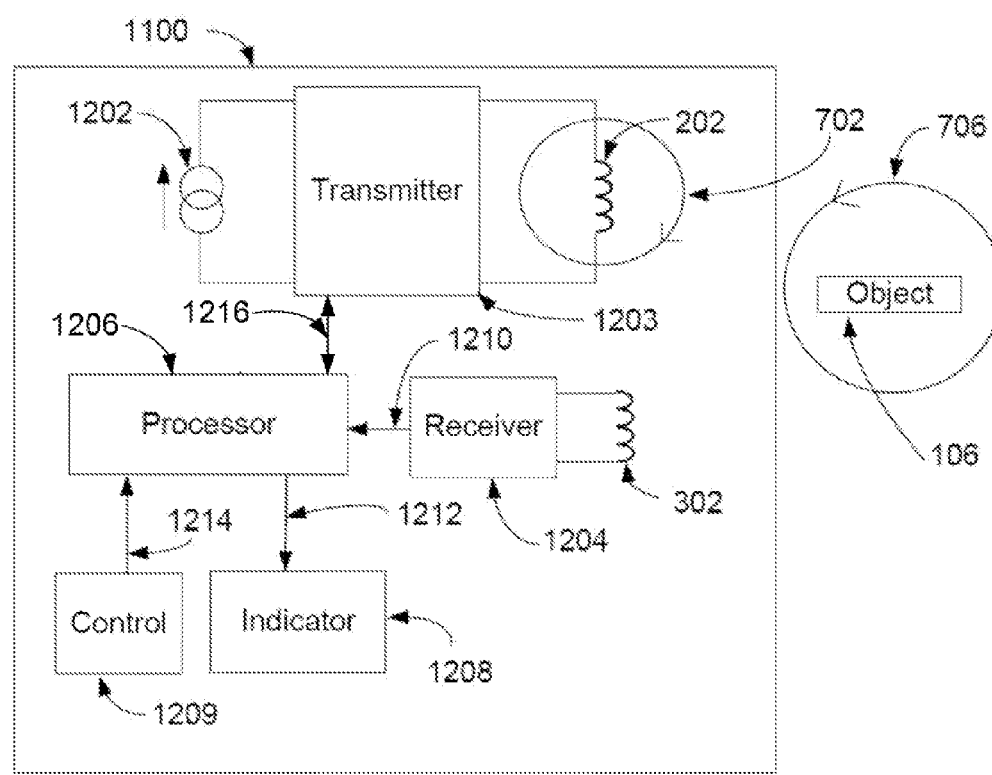
FIG. 12 illustrates a schematic of an example handheld detector device, in accordance with an embodiment of the present invention.

FIG. 12 illustrates a schematic of an example handheld detector device, in accordance with an embodiment of the present invention.

Handheld detector device 1100 includes transmit coil 202, receive coil 302, a time-varying current source 1202, a transmitter portion 1203, a receiver portion 1204, a processor portion 1206 an indicator portion 1208 and a control portion 1209.

A first leg of time-varying current source 1202 is connected to a first input of transmitter portion 1203. A second leg of time-varying current source 1202 is connected to a second input of transmitter portion 1203. A first output of transmitter portion 1203 is connected to a first leg of transmit coil 202. A second output of transmitter portion 1203 is connected to a second leg of transmit coil 202.

First leg of receive coil 302 is connected to a first input of receiver portion 1204. A second leg of receive coil 302 is connected to a second input of receiver portion 1204.

Processor portion 1206 receives information from receiver portion 1204 via a communication channel 1210. Indicator portion 1208 receives information from processor portion 1206 via a communication channel 1212. Processor portion 1206 receives information from control portion 1209 via a communication channel 1214. Processor portion 1206 sends and receives information to and from transmitter portion 1203 via communication channel 1216.

Time-varying current source 1202 generates a time-varying electrical current.

Transmitter portion 1203 receives a time-varying electrical current and processes the received signal. As a non-limiting example, transmitter portion 1203 amplifies the received time-varying electrical current. As a non-limiting example, transmitter portion 1203 may provide transmit signal information to the processor portion 1206 for use as a reference signal.

Receiver portion 1204 receives an electrical signal associated with magnetic field received by receive coil 302. As a non-limiting example, receiver portion 1204 may amplify the received signal. Receiver portion 1204 may be configured for detecting changes in phase and/or amplitude of the received signal.

As a non-limiting example, processor portion 1206 performs operational codes controlling the operation of handheld detector device 1100. Furthermore, as non-limiting examples, processor portion 1206 may include demodulators, phase detectors, filters, ground balancing and digital frequency generation. Processor portion 1206 may be configured for detection of the received signal based on changes in phase and/or amplitude of the received signal. Processor portion 1206 may be configured to generate multiple digital frequencies as an input to the transmitter portion 1203, which replaces the time-varying current source 1202.

Indicator portion 1208 provides information associated with the status and operation of handheld detector device 1100. As a non-limiting example, indicator portion 1208 may provide an audible sound when an object has been detected, or a change in the audio frequency to indicate the signal strength of the detected object, or the position of the detected object. Non-limiting examples of configurations for indicator portion 1208 include Liquid Crystal Display (LCD).

Control portion 1209 receives information from a user for configuring the operation of handheld detector device 1100. Non-limiting examples of control provided by control portion 1209 include sensitivity, audible volume and audible tone, operating frequency, and number of operating frequencies.

Time-varying current source 1202 provides a continuous time-varying electrical current to transmit coil 202 in order to create the primary magnetic field as noted by magnetic flux lines 702.

Transmit coil housing 102, as described with reference to FIG. 1, is translated and rotated relative to receive coil housing 104 (FIG. 1), to obtain a small reception or null reception of magnetic field at the output of receiver portion 1204. Following determination of the configuration for small or null reception of magnetic field, transmit coil housing 102 is secured to receive coil housing 104. Securing of transmit coil housing 102 to receive coil housing 104 may be performed by any known method. Configuring transmit coil housing 102 with respect to receive coil housing 104 in this manner provides for reduced interference between the transmitted magnetic field and the received magnetic field.

The location and relative position of object 106 can be determined with respect to the orientation and position of transmit coil 202 and receive coil 302.

Receiver portion 1204 detects changes in the received signal's amplitude and/or phase caused by a change in the coupling between the coils as a result of object 106 disturbing the received magnetic field. Furthermore, the location of object 106 can be determined by moving search coil assembly 100 relative to object 106, such that the plane traversing transmit coil 202 is positioned to traverse from above object 106 to below object 106. Furthermore, this positioning of transmit coil 202 with respect to object 106 results in a change in amplitude and/or phase of the received signal associated with the received magnetic field. Once search coil assembly 100 is located such that object 106 is detected, an indication is presented via indicator portion 1208.

Search coil assembly 100 may be moved such that the plane traversing transmit coil 202, results in the largest change in signal amplitude and/or phase to be received by receiver portion 1204. The largest amplitude signal is induced in object 106 when transmit coil 202 is located within the same plane as object 106. The largest change in the phase relationship between the receive coil signal and the reference signal, typically the transmitted signal, occurs when the position of object 106 traverses the plane of the transmit coil 202. Furthermore, a lower amplitude and change in phase of the signal is received by receiver portion 1204 when the plane traversing transmit coil 202 is positioned such that the angle between the plane and object 106 is at approximately 90 degrees.

In other embodiments, received signal may be converted from analog to digital via an A/D converter. Furthermore, the digitized version of the received signal may be received and processed by a microcontroller.

In other embodiments, search coil assembly 100 (FIG. 1) may be configured with a transmit coil and two receive coils. The receive coils may be connected in series, with opposing polarities. The opposing polarities provide a differential signal. The differential signal is connected to the receiver to be amplified and processed.

In other embodiments with two receive coils, the coils may be connected to a differential amplifier for amplification and processing.

In other embodiments with two receive coils, the receive coils may be connected separately to the receiver. Furthermore, the receive coils may be connected to separate amplifier inputs. Furthermore, the received signal may be amplified and then provided to a differential amplifier. The differential amplifier may provide additional amplification and processing for signal detection.

In other embodiments with two receive coils, the receive coils may be connected separately to the receiver. Furthermore, the connections may be supplied to separate amplifier inputs. Furthermore, the signals may be amplified and provided to a multiplexed A/D converter or a multiplicity of A/D converters for conversion from analog to digital. The digitized signal may be provided to a microcontroller for processing.

In operation, a user configures the operation of handheld detector device 1100 via control portion 1209. Time-varying current source 1202 generates a time-varying electrical current. Time-varying electrical current is applied to transmit coil 202. Transmit coil 202 converts the received electrical current to magnetic flux lines 702. Magnetic flux lines 702 travel through the ambient surroundings and impinge on object 106. Object 106 receives magnetic flux lines 702 and an eddy current is generated. Eddy current generates magnetic flux lines 706. Magnetic flux lines 706 travel through the ambient surroundings and impinge on receive coil 302. Receive coil 302 receives magnetic flux lines 706 and converts the magnetic flux to an electrical current. The electrical current generates a voltage across the receive coil 302 and is amplified by receiver portion 1204. The received signal is communicated to the processor portion 1206. The processor portion 1206 processes the received signal and determines if object 106 has been detected Processor portion 1206 communicates the detection of an object to indicator portion 1208. User is presented with information associated with detection of object 106. As an example, a user is moving handheld detector device 1100 over the ground and handheld detector device 1100 detects the object and communicates the detection of the object to the user.

FIG. 12 illustrates a schematic of a handheld detector device where handheld detector device transmits and receives magnetic fields for performing detection of an object.

Figure 13:
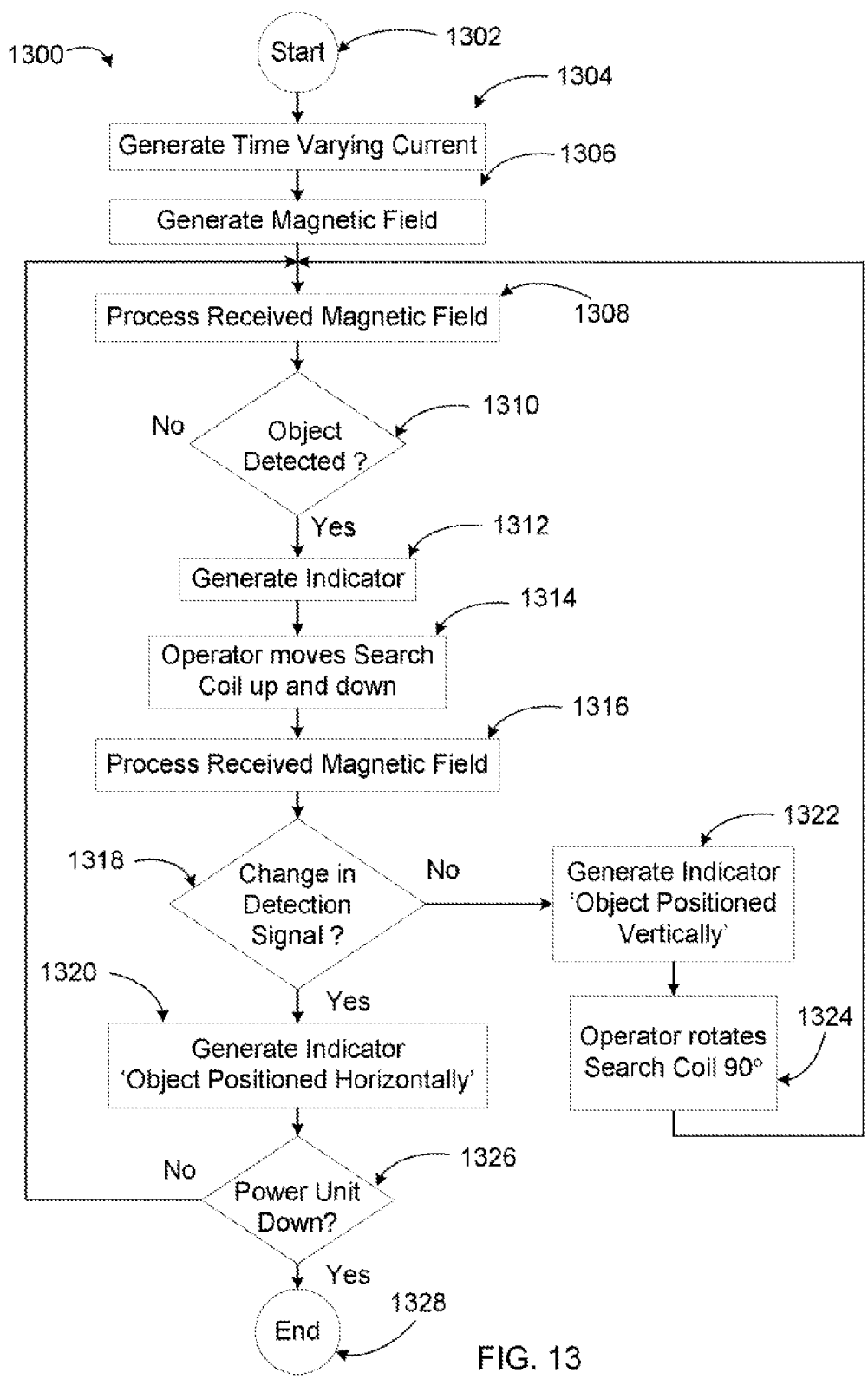
FIG. 13 illustrates an example method for operation of handheld detection device for performing detection, in accordance with an embodiment of the present invention.

FIG. 13 illustrates an example method for operation of handheld detection device for performing detection, in accordance with an embodiment of the present invention.

A method 1300 initiates in a step 1302.

Time-varying current source 1202 (FIG. 12) generates a time-varying electrical current in a step 1304 (FIG. 13).

Referring back to FIG. 13, then in a step 1306 a magnetic field is generated.

Transmit coil 202 (FIG. 12) receives time-varying current and generates magnetic flux lines 702 (FIG. 12).

Referring back to FIG. 13, then in a step 1308 processing is performed associated with detecting an object.

Magnetic flux lines 702 (FIG. 12) impinge on object 106 (FIG. 12). Object 106 receives magnetic flux lines 702 and generates an eddy current. The eddy current generates magnetic flux lines 706 (FIG. 12). Receive coil 302 (FIG. 12) receives magnetic flux lines 706 and converts magnetic flux to an electrical signal. The electrical signal is communicated to receiver portion 1204 (FIG. 12). Receiver portion 1204 receives electrical signal, amplifies the signal and communicates the received signal to processor portion 1206. Processor portion 1206 processes the received signal and determines if object 106 has been detected.

Referring back to FIG. 13, then in a step 1310, for a determination of detecting an object realized in step 1308, in a step 1312 an indication is generated. The processor portion 1206 (FIG. 12) communicates information to indicator portion 1208 (FIG. 12) associated with performing notification of detecting an object.

Referring back to FIG. 13, then in a step 1310, for a determination of not detecting an object in step 1308, in a step 1308 the received magnetic field is processed.

When the operator is notified that an object has been detected in step 1312, the operator moves the search coil assembly 100 (FIG. 1) in step 1314 (FIG. 13). Referring to FIG. 1, the search coil assembly 100 is moved by the operator up and down along the Y-Axis.

Referring back to FIG. 13, then in step 1316 processing is performed associated with detecting an object.

In a step 1318, for a determination of a change in the detection signal of an object realized in step 1316, in a step 1320 an indication is generated indicating the signal strength and position of the object relative to the search coil assembly. The object 106 shown in FIG. 1 will generally be positioned along the z axis at a tangent to the transmit coil housing 102 as shown in FIG. 1.

In a step 1318, for a determination of not detecting a change in the received signal, then in a step 1322 an indication is generated indicating the signal strength and position of the object relative to the search coil assembly. The object 106 shown in FIG. 1 will generally be positioned along the y axis at a tangent to the transmit coil housing 102.

As a non-limiting example the operator rotates the search coil assembly by 90 degrees in a step 1324 (FIG. 13). In other non-limiting examples, the operator may rotate the search coil assembly in smaller increments, to determine the precise position of the detected object. Referring to FIG. 1, the search coil assembly 100 is rotated by 90 degrees around the x axis. Referring back to FIG. 13, the received magnetic field is processed in a step 1308.

In a step 1326, for a determination of the unit being powered down by the operator, then in a step 1328 method 1300 terminates.

In a step 1326, for a determination of the unit not being powered down by the operator, then in a step 1308 the received magnetic field is processed. The operator continues searching for the object 106.

FIG. 13 illustrates an example method for operation of handheld detection device for performing detection where a time-varying current is generated, a magnetic field is transmitted, a return magnetic field is generated, processing is performed for detecting an object and an indication is presented associated with detecting an object.

Figure 14:
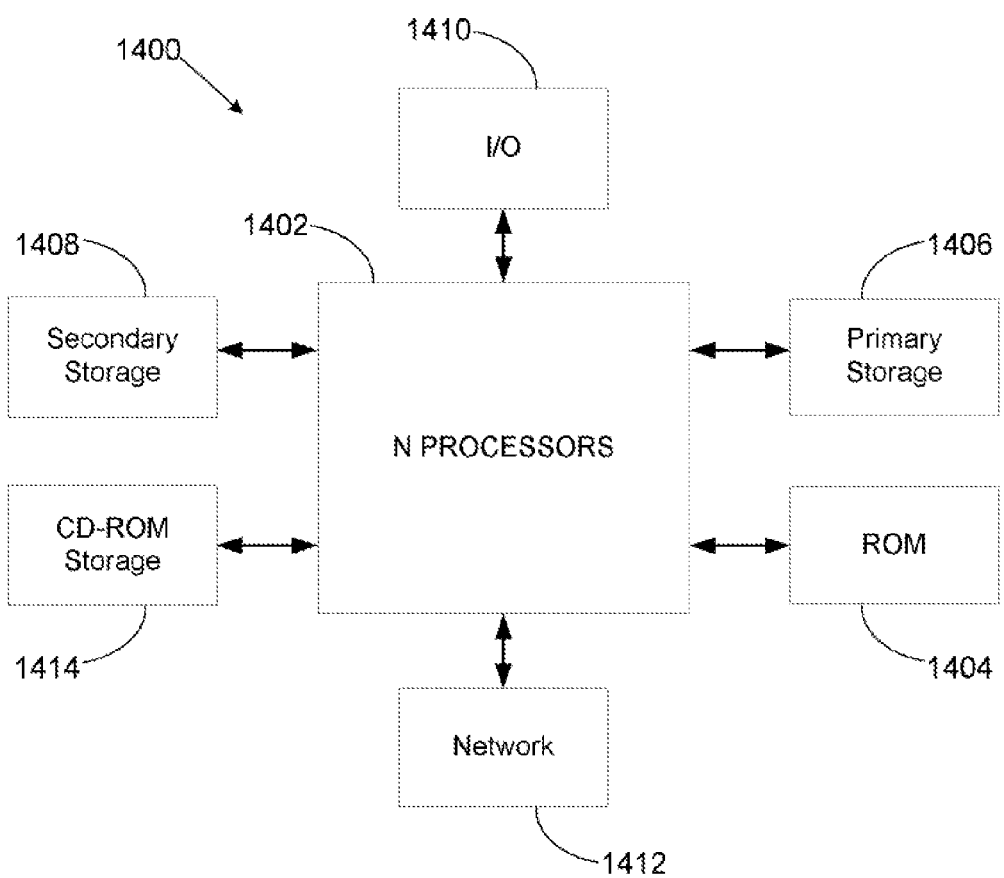
FIG. 14 illustrates a typical computer system that, when appropriately configured or designed, may serve as a computer system for which the present invention may be embodied.

FIG. 14 illustrates a typical computer system that, when appropriately configured or designed, may serve as a computer system 1400 for which the present invention may be embodied.

Computer system 1400 includes a quantity of processors 1402 (also referred to as central processing units, or CPUs) that may be coupled to storage devices including a primary storage 1406 (typically a random access memory, or RAM), a primary storage 1404 (typically a read-only memory, or ROM). CPU 1402 may be of various types including microcontrollers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors. As is well known in the art, primary storage 1404 acts to transfer data and instructions uni-directionally to the CPU and primary storage 1406 typically may be used to transfer data and instructions in a bi-directional manner. The primary storage devices discussed previously may include any suitable computer-readable media such as those described above. A mass storage device 1408 may also be coupled bi-directionally to CPU 1402 and provides additional data storage capacity and may include any of the computer-readable media described above. Mass storage device 1408 may be used to store programs, data and the like and typically may be used as a secondary storage medium such as a hard disk. It will be appreciated that the information retained within mass storage device 1408, may, in appropriate cases, be incorporated in standard fashion as part of primary storage 1406 as virtual memory. A specific mass storage device such as a CD-ROM 1414 may also pass data uni-directionally to the CPU.

CPU 1402 may also be coupled to an interface 1410 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 1402 optionally may be coupled to an external device such as a database or a computer or telecommunications or internet network using an external connection shown generally as a network 1412, which may be implemented as a hardwired or wireless communications link using suitable conventional technologies. With such a connection, the CPU might receive information from the network, or might output information to the network in the course of performing the method steps described in the teachings of the present invention.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of metal detector according to the present invention will be apparent to those skilled in the art. The invention has been described above by way of illustration, and the specific embodiments disclosed are not intended to limit the invention to the particular forms disclosed. For example, the particular implementation of the coils may vary depending upon the particular type geometric shape used. The coils described in the foregoing were directed to circular implementations; however, similar techniques using elliptical implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A search coil assembly comprising:
    a transmit coil being configured for radiating a magnetic field in response to a time varying electrical current,
        said transmit coil comprising a conductive path being disposed at least in a transmit plane for radiating the magnetic field;
    at least one receive coil being configured for inducting an electrical current in response to a time varying magnetic field,
        said receive coil comprising a conductive path being disposed at least in a receive plane for inducting the electrical current,
        said receive coil being configured to place said receive plane and said transmit plane in a substantially orthogonal orientation with said receive plane being substantially in null regions of said transmit coil's magnetic field, in which a metallic object, at a distance from the search coil assembly, substantially reacts to a radiated magnetic field from said transmit coil,
        and said receive coil inducts an electrical current in response to the reaction; and
    a conductive layer being disposed about said at least one receive coil,
        in which said transmit coil and receive coil are enclosed with separate housing structure,
        wherein said conductive layer is an enclosure formed by a mesh of conducting material.

2. The search coil assembly as recited in claim 1, further comprising:
    a transmit coil housing being configured for supporting said transmit coil in said transmit coil housing; and
    a receive coil housing being configured for supporting said receive coil in said receive coil housing.

3. The search coil assembly as recited in claim 1, further comprising a magnetic shielding material disposed proximate an intersection of said transmit plane and said receive plane.

4. The search coil assembly as recited in claim 1, wherein said conductive layer being disposed about said at least one receive coil being configured as a Faraday shield.

5. The search coil assembly as recited in claim 2, further comprising an isolation material being configured for thermally separating at least said transmit coil from said transmit coil housing.

6. The search coil assembly as recited in claim 1, further comprising at least a second receive coil, said second receive coil being substantially disposed in said receive plane.

7. The search coil assembly as recited in claim 6, in which said at least one receive coil and said second receive coil overlap at an intersection of said receive plane and said transmit plane.

8. The search coil assembly as recited in claim 6, in which said at least one receive coil and said second receive coil each comprises a semi-circular shape.

9. The search coil assembly as recited in claim 1, in which said at least one receive coil and said transmit coil each comprises a circular shape.

10. The search coil assembly as recited in claim 9, in which said transmit coil comprises a smaller diameter than a diameter of said at least one receive coil.

11. The search coil assembly as recited in claim 1, in which said conductive path of said transmit coil comprises a plurality of coil windings.

12. A system consisting of:
a search coil assembly comprising:
means being configured for radiating a magnetic field in response to a time varying electrical current,
    said radiating means being disposed at least in a transmit plane for radiating the magnetic field;
means being configured for supporting said radiating means;
means being configured for thermally separating at least said radiating means from said supporting means;
means being configured for inducting an electrical current in response to a time varying magnetic field,
    said inducting means being disposed at least in a receive plane for inducting the electrical current,
    said inducting means being configured to place said receive plane and said transmit plane in a substantially orthogonal orientation with said receive plane being substantially in null regions of said radiating means's magnetic field;
means being configured for supporting said inducting means;
means being configured for magnetically shielding proximate an intersection of said transmit plane and said receive plane; and
means, being disposed about said inducting means, and being configured for operating as a Faraday shield;
means being configured for positioning said search coil assembly during operation of the system; and
a control unit comprising:
means for enclosing;
means being configured for supplying the time varying electrical current to said radiating means;
means being configured for receiving the electrical current from said inducting means;
means being configured for communicating information associated with the status and operation of the system; and
means being configured for controlling said radiating means, processing signals at least from said inducting means and conveying the information to said communicating means,
    in which a metallic object, at a distance from the search coil assembly, reacts to a radiated magnetic field from said radiating means,
    said inducting means inducts an electrical current in response to the reaction, and the communicating means communicates the reaction.

13. A system comprising:
a search coil assembly comprising:
a transmit coil being configured for radiating a magnetic field in response to a time varying electrical current, said transmit coil comprising a conductive path being disposed in a transmit plane for radiating the magnetic field;
a transmit coil housing being configured for supporting said transmit coil in said transmit coil housing;
an isolation material being configured for thermally separating at least said transmit coil from said transmit coil housing;
at least one receive coil being configured for inducting an electrical current in response to a time varying magnetic field,
    said receive coil comprising a conductive path being disposed in a receive plane for inducting the electrical current, said receive coil being configured to place said receive plane and said transmit plane in a substantially orthogonal orientation with said receive plane being substantially in null regions of said transmit coil's magnetic field;
a receive coil housing being configured for supporting said receive coil in said receive coil housing;
a magnetic shielding material disposed proximate an intersection of said transmit plane and said receive plane; and
a conductive layer being disposed about said at least one receive coil,
    said conductive layer being configured as a Faraday shield;
a shaft being into engagement with said search coil assembly,
    said shaft comprising a handle and an arm cuff being configured for positioning said search coil assembly during operation of the system; and
a control unit comprising:
a control enclosure being into engagement with said shaft;
a transmitter unit being configured for supplying the time varying electrical current to said transmit coil;
a receiver unit being configured for receiving the electrical current from said receive coil;
an indicator unit being configured for communicating information associated with the status and operation of the system; and
a processor unit being configured for communicating with said transmitter unit, receiver unit, and said indicator unit,
    said processor unit being further configured for controlling said transmitter unit, processing signals at least from said receiver unit and conveying the information to said indicator unit,
    in which a metallic object, at a distance from the search coil assembly, reacts to a radiated magnetic field from said transmit coil,
    said receive coil inducts an electrical current in response to the reaction, and the indicator unit communicates the reaction.

14. The system as recited in claim 13, in which said control unit further comprises a control portion for substantially configuring the operation of the system.

15. The system as recited in claim 13, in which said search coil assembly further comprises a second receive coil, said second receive coil being disposed in said receive plane.

16. The system as recited in claim 15, in which said at least one receive coil and said second receive coil overlap at an intersection of said receive plane and said transmit plane.

17. The system as recited in claim 15, in which said at least one receive coil and said second receive coil each comprises a semi-circular shape.

18. The system as recited in claim 13, in which said at least one receive coil and said transmit coil each comprises a circular shape.

19. The system as recited in claim 13, in which said transmit coil comprises a substantially smaller diameter than a diameter of said at least one receive coil.

20. The system as recited in claim 13, in which said conductive path of said transmit coil comprises a plurality of coil windings.

* * * * *